US008444845B2

(12) United States Patent
Busch

(10) Patent No.: US 8,444,845 B2
(45) Date of Patent: May 21, 2013

(54) BIOFUEL COMPOSITION AND MANUFACTURING PROCESS

(76) Inventor: Rainer Busch, Reno, NV (US)

( * ) Notice: Subject to any disclaimer, the term of this patent is extended or adjusted under 35 U.S.C. 154(b) by 182 days.

(21) Appl. No.: 12/678,062

(22) PCT Filed: Sep. 12, 2008

(86) PCT No.: PCT/US2008/010707
§ 371 (c)(1),
(2), (4) Date: Oct. 21, 2010

(87) PCT Pub. No.: WO2009/035689
PCT Pub. Date: Mar. 19, 2009

(65) Prior Publication Data
US 2011/0035995 A1    Feb. 17, 2011

Related U.S. Application Data

(60) Provisional application No. 60/993,715, filed on Sep. 12, 2007.

(51) Int. Cl.
C25B 3/00           (2006.01)
(52) U.S. Cl.
USPC ........................................ 205/455; 205/462
(58) Field of Classification Search
USPC ................................................ 205/455, 462
See application file for complete search history.

(56) References Cited

U.S. PATENT DOCUMENTS

| | | | |
|---|---|---|---|
| 2,760,926 A * | 8/1956 | Kronenthal | 205/455 |
| 3,932,616 A * | 1/1976 | Meresz et al. | 585/16 |
| 4,119,506 A | 10/1978 | Bashforth | |
| 4,180,384 A | 12/1979 | Rice | |
| 4,340,705 A * | 7/1982 | Lal et al. | 526/139 |
| 2001/0019020 A1* | 9/2001 | Merk et al. | 205/413 |
| 2003/0183554 A1* | 10/2003 | Bazzani et al. | 208/16 |
| 2007/0039239 A1 | 2/2007 | Forester et al. | |

FOREIGN PATENT DOCUMENTS

| | | |
|---|---|---|
| DE | 138442 | 5/1901 |
| WO | 2007027669 | 3/2007 |
| WO | 2007/095215 | 8/2007 |

OTHER PUBLICATIONS

Schafer, "Recent Contributions of Kolbe Electrolysis to Organic Synthesis", Topics in Current Chemistry (no month, © 1990), vol. 152, pp. 92-151.*

Klocke et al., "Electroorganic Synthesis. 55. Influences on the Selectivity of the Kolbe versus the Non-Kolbe Electrolysis in the Anodic Decarboxylation of Carboxylic Acids", Chemische Berichte (no month, 1993), vol. 126, No. 7, pp. 1623-1630.*

Tajima et al., "Development of an Electrolytic System for Non-Kolbe Electrolysis Based on the Acid-Base Reaction Between Carboxylic Acids as a Substrate and Solid-Supported Bases", J. Am. Chem. Soc. (no month, 2007), vol. 129, pp. 6680-6681.*

(Continued)

Primary Examiner — Edna Wong
(74) Attorney, Agent, or Firm — Hovey Williams LLP

(57) ABSTRACT

A process for producing a fuel, which comprises the step of performing electrolysis on an alcoholic solution or a melt of a fatty acid or salt thereof or fatty acid ester or other derivative or precursor thereof, to decarboxylate said fatty acid or derivative, and produce a mixture of an ether and an alkene.

11 Claims, 1 Drawing Sheet

OTHER PUBLICATIONS

Kyriacou, "Modern Electroorganic Chemistry," 1994, Springer, Berlin Heidelberg, ISBN: 3540575049, Chapter on "Anodic Reactions 2.7 Carboxylic Acids," pp. 47-52.

Ed. Hammerich and Lund, "Organic Electrochemistry," 2000, CRC Press, ISBN: 0824704304, Chapter 14 by Torii and Tanaka on "Carboxylic Acids," pp. 499-543.

Torii et al., "Electrolytic Decarboxylation Reactions. I. Electrosyntheses of y-Substituted Butyrolactones and y-Substituted a,b-Butenolides from y-Substituted Paraconic Acids," J. Org. Chem., vol. 39, No. 17, pp. 2486-2488.

* cited by examiner

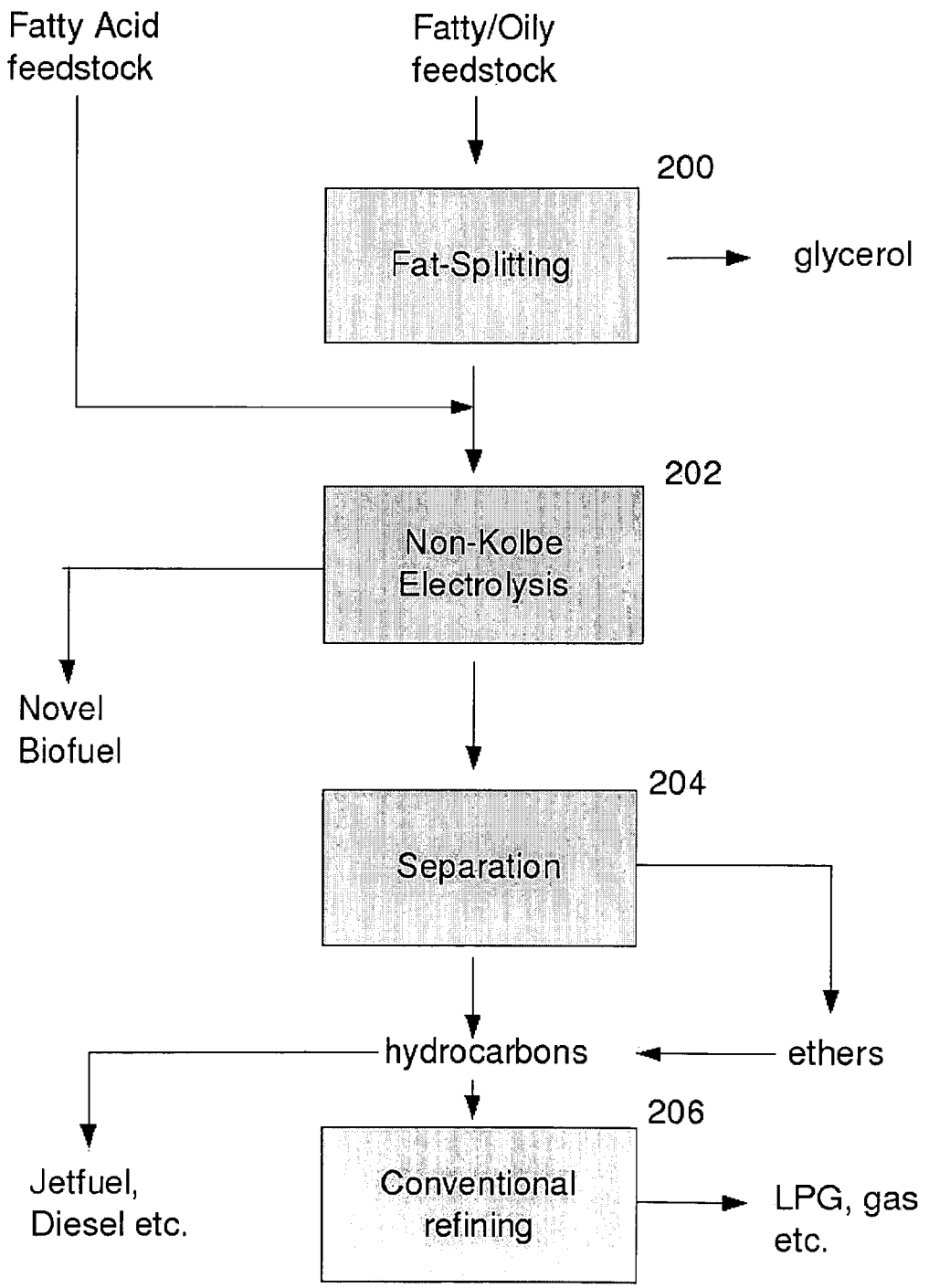

BIOFUEL COMPOSITION AND MANUFACTURING PROCESS

RELATED APPLICATIONS

This application is a national stage application, under 35 U.S.C. §371, of International Patent Application No. PCT/US2008/010707, filed Sep. 12, 2008, and published as WO 2009/035689, on Mar. 19, 2009, which claims the priority benefit of U.S. Provisional Application No. 60/993,715, filed Sep. 12, 2007, both of which are hereby incorporated by reference in their entirety.

FIELD OF THE INVENTION

The invention relates to a process for producing a fuel from fatty acids. It also concerns novel ether and novel alkene compounds, and the use of ethers and/or alkenes as fuels. The invention is particularly concerned with the field of biofuel alternatives to petroleum-based fuels, which are becoming increasingly scarce and costly. The fuels of the invention may be regarded as second generation biofuels and/or additives that have advantageous properties for storage and transportation, have lower cold flow pour points, good performance and safety, utilize renewable (sustainable) materials as a feedstock, burn more cleanly, preserve fossil fuels, are carbon neutral to a high degree, and, most importantly, can easily be adopted by most existing engine designs.

BACKGROUND OF THE INVENTION

Biodiesel and bioethanol are the main biofuels that are currently available for commercial use. These biofuels can be easily manufactured from renewable feedstock (e.g. biomass) with existing technology. However, many applications that use standard fuels cannot easily be converted to use biodiesel or bioethanol. There are differences in the physical and chemical properties of biodiesel and bioethanol compared to standard fuels, such as differences in energy density, flammability, boiling point range (or lack thereof), shelf life and solvent properties. The specification of the fuel that may be used with many engines is very specific and may not permit the use of existing biofuel alternatives, such as biodiesel and bioethanol. There is therefore a need for new, alternative biofuels and processes for producing the biofuels economically on an industrial scale.

Electrolysis is known in the art as a method for performing chemical reactions on a laboratory scale. Laboratory experiments where a normal Kolbe-reaction is prevented by drastically changed reaction conditions have been performed for more than 100 years, beginning with Moest et. al. (German patent 138442, issued 1903) who created alcohols, aldehydes and ketones from fatty acids using electrolysis. His research was late honoured by naming this type of electrochemical decarboxylation after him ("Hofer-Moest reaction") and it spawned numerous other interesting applications in the chemical literature, none of which, however, has achieved any degree of commercial significance.

A comprehensive overview of the scientific background of this invention can be found in "Organic Electrochemistry" by Henning Lund, Manuel M. Baizer, Ole Hammerich, Chapters 12/14, ISBN: 0824704304 by CRC Press. Kronenthal et al focussed on aliphatic ethers, and on methoxy-undecane in particular (U.S. Pat. No. 2,760,926, issued in 1956), but achieved yields of 40% or less while consuming large amounts of electricity (by at least a factor ten judging from the voltage applied (90+ Volts). Use of these, or any other similar ethers, in a mix with hydrocarbons for fuels as suggested here, finds no mention in the literature.

More recently, however, in WO 2007/095215 and WO 2007/027669 the original Kolbe-reaction was quoted as a means, among numerous other techniques, to create useful hydrocarbons utilizing fatty acids of renewable origin. However due to the nature of the Kolbe-reaction, the chain length would almost double in the process, creating a mix of C30-C34 hydrocarbons that would need extensive conventional refining to yield useable, liquid transportation fuels. This may be contrasted with a one-step specialized Hofer-Moest process.

It would be possible to manufacture said liquid fuels by means of a regular, crossed Kolbe-electrolysis, e.g. using oleic acid and acetic acid as feedstock. This procedure would yield a C18-hydrocarbon and would maintain the desired cis-/"Z-" configuration of the double bond. However, it is believed that such a technique would be far less economical due to the consumption of acetic acid, the costly use of platinum anodes, and the low-value byproducts.(i.e. ethane and a doubly unsaturated C34 hydrocarbon in this case) generally unavoidable in a crossed Kolbe reaction.

It has been reported that oil companies cooperating with producers of animal fat and/or vegetable oil create hydrocarbons from triglycerides, making straight C16/C18 alkanes and propane (from the glycerol contained in fats/oils). However, this process uses a catalyst and totally hydrogenates feedstock at high pressures and temperatures. It consumes large amounts of hydrogen and destroys all special cis/"Z-" oriented double bonds. The process described in this application can preserve such double bonds and can generate hydrogen as a by-product.

SUMMARY OF THE INVENTION

In a first aspect, the invention provides a process for producing a fuel, which fuel may be, for example, a second-generation biofuel. The process may also be used to manufacture conventional hydrocarbon fuels from renewable feedstocks.

In particular, in a first aspect the invention provides a process for producing a fuel, which comprises the step of performing electrolysis on an alcoholic solution or a melt of a fatty acid or salt thereof or fatty acid ester or other derivative or precursor thereof; to decarboxylate said fatty acid or derivative thereof, and produce a mixture of an ether and an alkene.

By a precursor of a fatty acid (or of a salt or other derivative thereof) we refer to a compound that will produce such a material under appropriate reaction conditions, in particular under the conditions under which electrolysis is to be carried out. An example of a suitable precursor is an ester that hydrolyses in situ.

The invention also provides a product produced directly or indirectly by this process.

The ether and alkene mixture that is produced may be used to prepare a fuel.

The process of the invention may further comprise the step of purifying/separating the mixture of alkene and ether from the alcoholic solution. Additionally, or alternatively, the process of the invention may further comprise the step of adding one or more fuel additives to the fuel.

Decarboxylation of the carboxylic acid group of the fatty acid by electrolysis generates an alkyl radical intermediate. It is possible, under some reaction conditions, for the Kolbe reaction to occur, whereby the radical dimerises by reaction with another alkyl radical of the same type to produce a long-chain alkane. However, the conditions used for electrolysis in the process of the invention are selected to generate a low concentration of free radicals, which minimises the occurrence of free radical dimerisation and thereby reduces or prevents the Kolbe reaction.

In the process of the invention, the free radicals generated by decarboxylation of the fatty acid either react with a nearby solvent molecule to form an ether or to eliminate a hydrogen atom to form an alkene. In principle, the radicals could also be further oxidized (i.e. loose another electron) and become carbocations, which may undergo structural changes before either reacting with the solvent to form an ether or eliminating a hydrogen atom to form an alkene. An isomeric mixture of ethers and an isomeric mixture alkenes are sometimes obtained from the process of the invention. The number of carbon atoms in the alkenes is one less than the number of carbon atoms in the fatty acid (the carboxyl group of the fatty acid splits off as $CO_2$).

A number of factors may influence the nature and concentration of the radicals that are produced during the electrolysis step. These factors include the size and shape of the electrodes, the material from which the electrodes are made, the distance separating the electrodes in solution, the electrolyte and solvent that are used, the concentration of the fatty acid, the type of current (direct or alternating) and the current density. Thus, the electrolysis step may be performed in a number of different ways in order to obtain the desired products and to minimise Kolbe couplings. The conditions also influence the amounts of ether and alkene that are produced.

Electrolysis may be performed using a relatively low current density. Typically, the electrolysis is performed using a current density of 0.01 to 0.2 $Acm^{-2}$. It is preferred that the current density be 0.02 to 0.15 $Acm^{-2}$, particularly 0.05 to 1.0 $Acm^{-2}$, more preferably 0.06 to 0.09 $Acm^{-2}$ most preferably 0.07 to 0.08 $Acm^{-2}$. We usually prefer to employ a low voltage, for example less than 15 V, particularly less than 12 V, for example about 10 V. The voltage may be chosen to achieve a balance between economy (at low voltage) and avoidance of by-products (at high voltages).

A relatively low current density may be achieved in any suitable way, for example by selecting appropriate electrode distance, electrolyte concentration and/or cell voltage.

The anode and cathode of the apparatus used to perform electrolysis may be composed of materials that are the same as or different from one another, and each may be independently selected from carbon, platinum, steel, copper, silver, gold and nickel. If the anode and/or cathode comprises carbon, then it is preferred that it comprise graphite.

In one embodiment of the invention, the anode is composed of a material other than graphite.

In another embodiment of the invention both the anode and cathode are composed of the same material. In this embodiment it is preferred that they both comprise graphite.

Whilst the material of the electrodes is often not critical, the surface characteristics will in general be important. We prefer that the electrodes have a rough surface, such as that provided by graphite rather than the smooth or glassy surface usually provided by, say, platinum. We believe that this gives reaction intermediates the chance to react at the surface of the electrodes. A composite electrode could be provided having a highly conductive core of one material and a coating of a material of a suitable roughness. Also, a usually smooth material could be treated to produce the desired roughness.

The anode and cathode of the apparatus in which electrolysis is to be performed may be arranged in such a manner that when they are placed in the alcoholic solution, the closest spacing between the anode and cathode in the alcoholic solution is from 0.5 to 5 mm. It is preferred that the closest spacing between the anode and cathode in solution is from 1 to 2 mm.

The electrolysis step in the process of the invention is typically carried out on an alcoholic solution of a fatty acid, or salt or other derivative thereof, where the total concentration of the fatty acid and/or derivative in the alcoholic solution is usually at least 0.5 M, more usually at least 0.8 M, for example about 1 M. The precise value will often depend on the ability of a solvent to keep the material in solution.

In principle any alcohol may be used as the solvent for the electrolysis process, provided that it is a liquid at the temperature at which the reaction is to be performed. It is preferred that the alcohol is allyl alcohol, crotyl alcohol or a saturated, linear or branched alkyl alcohol (particularly a $C_1$-$C_{11}$ alkyl alcohol). Alkyl alcohols are more preferred, especially saturated, linear or branched $C_1$-$C_5$ alkyl alcohols. Alcohols that are particularly suitable include methanol, ethanol, n-propanol, i-propanol, n-butanol, s-butanol or t-butanol, especially methanol, ethanol and n-propanol.

It is not essential for the alcoholic solution to be anhydrous. Up to 15% by volume of the solution may be water, more typically up to 10% by volume, and more preferably up to 5% by volume. In another embodiment, the alcoholic solution is anhydrous.

The alcoholic solution of the fatty acid, or salt thereof, may comprise an alkali metal or alkaline earth metal hydroxide salt (especially LiOH, NaOH, KOH or in some situations $CaOH_2$ although the latter material may have insufficient solubility in some solvents). A concentration of at least 0.5 M, preferably at least 0.8 M, particularly about 1 M will usually be suitable to achieve the desired current density, the metal ions being the principle charge carriers during electrolysis. If a fatty acid is initially added to the alcoholic solution, then the alkali metal or alkaline earth metal hydroxide salt may be added to deprotonate the fatty acid in situ. The hydroxide salt is not in general added to increase electrical conductivity of the solution. In one embodiment of the process, electrically conductive inorganic salts, particularly alkali metal (especially sodium and potassium) chlorides, sulfates, persulfates, perchlorates, carbonates and acetates are excluded from the alcoholic solution.

The electrolysis step generates heat and will heat the alcoholic solution and may cause reflux of the solvent. It is preferred that electrolysis be performed at the reflux temperature of the alcoholic solvent. It will usually be satisfactory to carry out the electrolysis at atmospheric pressure. In some situations, however, a high pressure might be desirable in order to allow a higher temperature to be used without excessive bubbling.

The process of the invention converts a fatty acid, or salt etc. thereof, into a mixture of an alkene and an ether. The term fatty acid as used herein refers to an organic compound having a single carboxylic acid attached to an aliphatic chain, which may be branched or unbranched and may be saturated or unsaturated. Typically, the fatty acid has at least 8 carbon atoms. It is preferred that the aliphatic chain of the fatty acid is unbranched.

Suitable unbranched saturated fatty acids include one or more of butanoic acid, pentanoic acid, hexanoic acid, heptanoic acid, octanoic acid, nonanoic acid, decanoic acid, undecanoic acid, dodecanoic acid, tridecanoic acid, dodecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid.

Suitable monounsaturated fatty acids include one or more of cis-5-dodecenoic acid, myristoleic acid, palmitoleic acid, oleic acid, eicosenoic acid, erucic acid, and nervonic acid. Suitable polyunsaturated fatty acids include linoleic acid, α-linoleic acid, linolenic acid, arachidonic acid, eicosapentaenoic acid, and docosahexaenoic acid.

The term salt of a fatty acid refers to the carboxylate salts of the fatty acid (e.g. sodium heptanoate). The counter cation to the carboxylate anion is typically an alkali metal cation, an alkaline earth metal cation, ammonium or alkylated ammonium ($NR_4$ where each R is independently a C1-4 alkyl group). In particular, the counter cation is preferably selected from one or more of lithium, sodium, potassium, rubidium, and ammonium. More preferably, the counter cation is sodium or potassium.

In one embodiment of the invention, the use of alkali metal salts of propionic acid (particularly sodium propionate), caprylic acid (particularly potassium caprylate), lauric acid (particularly sodium laurate), myristic acid (particularly sodium myristate), oleic acid (particularly potassium oleate), stearic acid (particularly potassium stearate), tridecanoic acid (particularly potassium tridecanoate), pentadecanoic acid (particularly potassium pentadecanoate), heptadecanoic acid (particularly potassium heptadecanoate) as the fatty acid, or salt thereof, are excluded.

In one embodiment, the fatty acid, or salt etc. thereof, is unsaturated, more preferably is monounsaturated. It has been surprising found that the electrolysis process of the present invention retains the configuration of the double bonds in the alkyl chain of the fatty acid after they have been decarboxylated. When the fatty acid, or salt thereof, is unsaturated (monounsaturated or polyunsaturated), it is preferred that there is at least one double bond having the cis/Z configuration. Preferably, the fatty acid, or salt etc. thereof, is monounsaturated and has a double bond having the cis/Z configuration. More preferably, the fatty acid is oleic acid.

Analysis of experimental results reveals that each of the ether and the alkene components is formed during the reaction in a ratio of approximately 50:50 with straight chain saturated fatty acids. This ratio varies significantly, however, depending on the fatty acids involved, as well as on the reaction conditions.

A further aspect of the invention relates to novel ether compounds.

Thus, in a second aspect the invention provides a compound represented by formula (I):

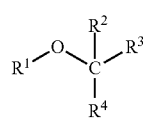

(I)

wherein:
$R^1$ is an allyl group, a crotyl group or a saturated, linear or branched $C_1$-$C_5$ alkyl group;
$R^2$ is hydrogen or a linear, saturated $C_1$-$C_4$ alkyl group;
$R^3$ is hydrogen or a linear, saturated $C_1$-$C_4$ alkyl group;
$R^4$ is a linear or branched, saturated or unsaturated $C_3$-$C_{21}$ alkyl group;
and wherein the sum of the number of carbon atoms in the $R^2$, $R^3$ and $R^4$ groups is from 6 to 21;
except for the compounds represented by formula (I) when:
(i) $R^1$ is a methyl group, both $R^2$ and $R^3$ are hydrogen and $R^4$ is a linear, saturated $C_6$-$C_{15}$, $C_{17}$, $C_{19}$ or $C_{21}$ alkyl group;
(ii) $R^1$ is an ethyl group, both $R^2$ and $R^3$ are hydrogen and $R^4$ is a linear, saturated $C_6$, $C_7$, $C_9$, or $C_{11}$ alkyl group;
(iii) $R^1$ is a methyl group, $R^2$ is hydrogen, $R^3$ is a methyl group and $R^4$ is a linear, saturated $C_5$-$C_{13}$ or $C_{15}$-$C_{16}$ alkyl group;
(iv) $R^1$ is a methyl group, $R^2$ is hydrogen, $R^3$ is an ethyl group and $R^4$ is a linear, saturated $C_5$-$C_7$ alkyl group; and
(v) $R^1$ is an n-propyl group, $R^2$ is hydrogen, $R^3$ is an n-propyl group and $R^4$ is a linear, saturated $C_3$-$C_5$ alkyl group.

In one embodiment of the invention, compounds represented by formula (I) are excluded when:
(vi) $R^1$ is a methyl group, both $R^2$ and $R^3$ are hydrogen and $R^4$ is a linear, saturated $C_{16}$ alkyl group; and
(vii) $R^1$ is a methyl group, $R^2$ is hydrogen, $R^3$ is an ethyl group and $R^4$ is a linear, saturated $C_4$, $C_8$ or $C_{13}$ alkyl group.

In particular, compounds represented by formula (I) are excluded when:
(viii) $R^1$ is an n-butyl group, both $R^2$ and $R^3$ are hydrogen and $R^4$ is a linear, saturated $C_7$ alkyl group; and
(ix) $R^1$ is a t-amyl group, both $R^2$ and $R^3$ are hydrogen and $R^4$ is a linear, saturated $C_{15}$ alkyl group.

In some embodiments of the invention $R^1$ is a saturated, linear or branched $C_1$-$C_5$ alkyl group, preferably a saturated, linear $C_1$-$C_5$ alkyl group.

In general $R^1$ may be a methyl, ethyl, n-propyl, i-propyl, n-butyl, s-butyl or t-butyl group, more preferably a methyl, ethyl, n-propyl group, and most preferably an ethyl group.

In general $R^2$ may be hydrogen.

In general $R^3$ may be hydrogen, methyl, ethyl or n-propyl, and preferably is hydrogen, methyl or ethyl.

In general $R^4$ may be a linear or branched, saturated or unsaturated $C_5$-$C_{20}$ alkyl group, particularly a $C_7$-$C_{19}$ alkyl group, prefer a $C_8$-$C_{18}$ alkyl group, more preferably a $C_9$-$C_{17}$ alkyl group, most preferably a $C_{10}$-$C_{16}$ alkyl group.

In general $R^4$ may be a linear group.

In general $R^4$ may have an odd number of carbon atoms.

In general $R^4$ may be an unsaturated alkyl group having at least one carbon-carbon double bond, preferably at least one of the double bonds having the Z configuration.

The sum of the number of carbon atoms in the $R^2$, $R^3$ and $R^4$ groups may be from 8 to 20, preferably from 10 to 19, more preferably from 11 to 18, 12 to 17, and 13 to 16.

In general $R^4$ may be n-$C_{13}H_{27}$, n-$C_{15}H_{31}$ or n-(5Z)-$C_{15}H_{29}$.

Specific compounds of the invention include 1-(methoxy)-8Z-tridecene, 1-(ethoxy)-8Z-tridecene, 1-(propoxy)-8Z-tridecene, 1-(butoxy)-8Z-tridecene, 2-(methoxy)-8Z-tridecene, 2-(ethoxy)-8Z-tridecene, 2-(propoxy)-8Z-tridecene, 2-(butoxy)-8Z-tridecene, 3-(methoxy)-8Z-tridecene, 3-(ethoxy)-8Z-tridecene, 3-(propoxy)-8Z-tridecene, 3-(butoxy)-8Z-tridecene, 1-(methoxy)-8Z-pentadecene, 1-(ethoxy)-8Z-pentadecene, 1-(propoxy)-8Z-pentadecene, 1-(butoxy)-8Z-pentadecene, 2-(methoxy)-8Z-pentadecene, 2-(ethoxy)-8Z-pentadecene, 2-(propoxy)-8Z-pentadecene, 2-(butoxy)-8Z-pentadecene, 3-(methoxy)-8Z-pentadecene, 3-(ethoxy)-8Z-pentadecene, 3-(propoxy)-8Z-pentadecene, 3-(butoxy)-8Z-pentadecene, 1-(methoxy)-8Z-heptadecene, 1-(ethoxy)-8Z-heptadecene, 1-(propoxy)-8Z-heptadecene, 1-(butoxy)-8Z-heptadecene, 2-(methoxy)-8Z-heptadecene, 2-(ethoxy)-8Z-heptadecene, 2-(propoxy)-8Z-heptadecene, 2-(butoxy)-8Z-heptadecene, 3-(methoxy)-8Z-heptadecene, 3-(ethoxy)-8Z-heptadecene, 3-(propoxy)-8Z-heptadecene, 3-(butoxy)-8Z-heptadecene, 1-(methoxy)-10Z-nonadecene, 1-(ethoxy)-10Z-nonadecene, 1-(propoxy)-10Z-nonadecene, 1-(butoxy)-10Z-nonadecene, 2-(methoxy)-10Z-nonadecene, 2-(ethoxy)-10Z-nonadecene, 2-(propoxy)-10Z-nonadecene, 2-(butoxy)-10Z-nonadecene, 3-(methoxy)-10Z-nonadecene, 3-(ethoxy)-10Z-nonadecene, 3-(propoxy)-10Z-nonadecene and 3-(butoxy)-10Z-nonadecene.

In a third aspect the invention provides a compound represented by formula (III):

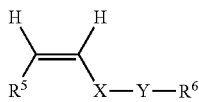

wherein:
$R^5$ is a saturated, linear $C_1$-$C_{19}$ alkyl group or an unsaturated, linear $C_2$-$C_{19}$ alkyl group;
X is a single bond or a —$(CH_2)_n$— group;
n is an integer from 1 to 18;
Y is a single bond or a —CH=CH— group;
$R^6$ is hydrogen, a saturated, linear $C_1$-$C_{17}$ alkyl group or a unsaturated, linear $C_2$-$C_{17}$ alkyl group; and
wherein the total number of carbon atoms in the compound represented by formula (III) is from 6 to 21.

In general $R^5$ may be a linear, saturated $C_1$-$C_{19}$ alkyl group, preferably $C_2$-$C_{18}$ alkyl, more preferably $C_3$-$C_{17}$ alkyl, most preferably $C_4$-$C_{16}$ alkyl. In general, and particularly for these embodiments, X is preferably a single bond and/or Y is a single bond and/or R6 is H.

In general $R^6$ may be hydrogen or a saturated, linear $C_2$-$C_{16}$ alkyl group, preferably a $C_4$-$C_{15}$ alkyl group, more preferably a $C_6$-$C_{14}$ alkyl group.

Preferably $R^6$ is hydrogen or a methyl, ethyl, n-propyl or n-butyl group, more preferably hydrogen, methyl, ethyl or n-propyl, and most preferably an ethyl group.

In general in other embodiments $R^6$ is a linear, unsaturated $C_4$-$C_{16}$ alkyl group, preferably $C_5$-$C_{15}$ alkyl group, more preferably $C_6$-$C_{14}$ alkyl group.

In general n is from 3 to 12, and preferably 5 or 9, when Y is a —CH=CH— group.

Specific compounds of this aspect of the invention include 1,8Z-tridecadiene, 2E,8Z-tridecadiene, 2Z,8Z-tridecadiene, 3E,8Z-tridecadiene, 3Z,8Z-tridecadiene, 4E,8Z-tridecadiene, 4Z,8Z-tridecadiene, 1,8Z-pentadecadiene, 2E,8Z-pentadecadiene, 2Z,8Z-pentadecadiene, 3E,8Z-pentadecadiene, 3Z,8Z-pentadecadiene, 4E,8Z-pentadecadiene, 4Z,8Z-pentadecadiene, 1,8Z-heptadecadiene, 2E,8Z-heptadecadiene, 2Z,8Z-heptadecadiene, 3E,8Z-heptadecadiene, 3Z,8Z-heptadecadiene, 4E,8Z-heptadecadiene, 4Z,8Z-heptadecadiene, 1,10Z-nonadecadiene, 2E,10Z-nonadecadiene, 2Z,10Z-nonadecadiene, 3E,10Z-nonadecadiene, 3Z,10Z-nonadecadiene, 4E,10Z-nonadecadiene and 4Z,10Z-nonadecadiene.

In a forth aspect the invention provides the use of a compound represented by formula (II):

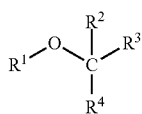

as a fuel, wherein:
$R^1$ is an allyl group, a crotyl group or a saturated, linear or branched $C_1$-$C_5$ alkyl group;
$R^2$ is hydrogen or a linear, saturated $C_1$-$C_4$ alkyl group;
$R^3$ is hydrogen or a linear, saturated $C_1$-$C_4$ alkyl group;
$R^4$ is a linear or branched, saturated or unsaturated $C_3$-$C_{21}$ alkyl group;

and wherein the sum of the number of carbon atoms in the $R^2$, $R^3$ and $R^4$ groups is from 6 to 21.

In the above use of the invention compounds represented by formula (II) are preferably excluded when:
(i) $R^1$ is a methyl group, both $R^2$ and $R^3$ are hydrogen and $R^4$ is a linear, saturated $C_6$-$C_9$, $C_{11}$, $C_{13}$, $C_{15}$ or $C_{17}$ alkyl group; and
(ii) $R^1$ is an ethyl group, both $R^2$ and $R^3$ are hydrogen and $R^4$ is a linear, saturated $C_6$, $C_7$, $C_9$, or $C_{11}$ alkyl group.

The present invention particularly provides such a use wherein the compound is as defined in the second or third aspects of the invention referred to above.

We prefer that these compounds constitute a fuel, rather than act solely or mainly as a fuel additive; and to that end we prefer that the ethers, the alkenes, or the ethers and alkenes together constitute at least 20% particularly at least 50%, preferably at least 70%, and more preferably at least 90% by weight of the total fuel composition.

Thus, in a fifth aspect, the invention provides a fuel composition comprising an ether compound represented by formula (I) or (II) as defined above.

In a sixth aspect the invention provides a fuel composition comprising an alkene compound represented by formula (I), (II) or (III) as defined above.

In particular, the amount of the ether, or the amount of alkene, or the amount of ether plus the amount of alkene, present may be for example at least 20% by weight of the composition, preferably at least 30, 40, 50, 60, 70, 80, 90 or 95%.

In the use or in the composition of the invention, the fuel composition may include one or more of a lubricity additive, combustion improver, detergent, dispersant, cold flow improver, dehazer, demulsifier, cetane improver, antioxidant, scavenger or a pollution suppressant.

The hydrocarbon or hydrocarbon chain can be derived from any suitable feedstocks, and in particular from any biomass feedstock or in any way from biomass. For example, the hydrocarbon or hydrocarbon chain can be derived from a saturated fatty acid, or salt or other derivative.

The composition can be formed by a process including electrolysis. Moreover, it can be formed by a process further including catalysis.

The electrolysis can be performed in a batch or continuous mode of operation.

The product may be a hydrocarbon-ether mix which may be subjected to one or more further processing steps including but not limited to distillation, catalysis and crystallization. Thus, the ether and the hydrocarbon may be further separated or purified and/or reacted. The result may be a pure hydrocarbon and/or pure ether useful as synthetic fuel components.

The core manufacturing process is preferably therefore a non-Kolbe electrolysis of fatty acid salts (for instance sodium, potassium), performed in solution in a lower alcohol (methanol, ethanol, isopropanol (IPA) etc.) using a simple electrolysis cell with, for example, two or more graphite electrodes with relatively small nominal spacing in between (~1 mm) and medium current density (less than approximately 0.05-0.1 A-cm$^{-2}$) under near reflux conditions, where evaporation heat can be used to discharge excess heat created by the current involved.

It is believed that electrolysis has not previously been used directly to create biofuels. In fact, such a process is today not used to create any fuels at any significant scale, let alone biofuels. Also, very few hydrocarbons are today being created commercially at any scale from biomass feedstocks, except using gasification and Fischer-Tropsch processes, which work very differently from electrolysis. Thus it is surprising indeed that electrolysis can be used to create biofuels.

Further technical details relating to preferred embodiments of the invention follow.

Ethers

An intermediate bio-fuel composition according to the present invention can have the following structure:

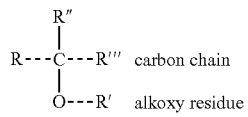

with an alkyl chain R, a single oxygen atom bonded to one of the primary or secondary carbon atoms within a hydrocarbon chain and another, shorter alkyl chain R' bonded to the oxygen atom.

The residues R, R" and R''' can represent one or more selected from the group consisting of a single H as well as any branched or unbranched, saturated or unsaturated alkyl group including, but not limited to methyl, ethyl, n-propyl, iso-propyl, allyl, all 4 butyls, E- or Z-crotonyl, neo-pentyl, all possible isoprenyls, octyls, nonyls, decyls, undecyls, dodecyls, tridecyls, tetradecyls, pentadecyls, pentadecenyls, hexadecyls, heptadecyls, heptadecenyls and heptadecadienyls.

The alkyl chain R' can be an alkoxyalkane and can comprise one or more selected from a group consisting of H, methyl, ethyl, propyl/iso-propyl, allyl, and all isomers of butyl, butenyl, pentyl, pentenyl and hexyl.

In one embodiment the inventions provides a composition is in accordance with formula (IV):

$$R-CR'R''-O-R''' \qquad (IV).$$

Formula (IV) can be further described as follows. The alkyl R—CR'—R" has a total number of carbon atoms in a range from 3 to 21 (i.e. short, medium or long chain alkyl group, saturated or unsaturated), and where R''' is selected from a small group consisting of H, Me, Et, iPr, Pr, nBu, iBu, sBu, tBu, etc. In other words, an alkoxyalkane, otherwise known as an ether.

Hydrocarbons are a main product of the core process. Ethers are the other products of the core process. Both are formed in varying amounts (less than 20% to more than 80% each). These ethers can be used together with those hydrocarbons as a novel fuel mixture, with properties similar to B20/50/80 (i.e. a 20/50/80% biodiesel/petroleum fuel mixture or sequence) while performing better (higher energy content, lower cold filter plugging point (CFPP), less aggressive solvent properties, etc.). In this case the core process need be the only process employed.

Alternatively, these ethers can be seen as intermediates that can be refined further, for instance into hydrocarbons using a catalytic process. The resulting products may be "pure" hydrocarbons (i.e. having no more than traces of other compounds). This is possible for applications where fuels containing ethers are unappealing for whatever reason. If catalytic processing is not desirable for any reason, the hydrocarbon/ether mixture can also be separated by means of conventional distillation or other suitable means.

Today there are no ethers commonly used in diesel type of formulations except dimethyl-ether (DME: $CH_3-O-CH_3$) which is a gas at room temperature and which is, at best, an experimental fuel. It can be derived from cellulosic biomass; however, the processes used are based on gasification and very different from the invented process in that, for example, gasification and associated processes used to form DME cannot easily produce other, for example longer-chain, ethers.

In contrast to prior art biodiesel formulations (the main renewable fuel for diesel engines) having two oxygen atoms per molecule, the present ethers preferably have only one oxygen atom per molecule, and thus have greater energy content. In other words, the energy density of prior art biodiesel fuel formulations is lower than that of the present biofuel formulations. Moreover, prior art biodiesel formulations have some undesirable properties, e.g. they act as solvents that attack rubber and other materials in engines, and they have a fairly high melting range (e.g. palm oil biodiesel without additives melts between 5 and 10° C.). In contrast, the present biofuel having ethers as their only non-hydrocarbon component in general act as very mild solvents at best, and they generally have a much lower melting range than biodiesel made from the same feedstock. This results in the present biofuel melting at or below approximately −30° C., well below—instead of above—the freezing point of water.

Also, the low oxygen content in the present biofuel helps making internal combustion more complete and thereby less toxic due to cleaner combustion.

The present fuel composition consisting mainly of HC's is also much closer to petroleum-based diesel fuel in terms of engine and distribution network compatibility as well as shelf life.

Alkenes

The invention also relates to a hydrocarbon composition comprising any unsaturated hydrocarbon, derived from any fatty acid or from any renewable source, utilizing any of the above or below described processes with or without variations with at least one double bond with cis- or "Z-" configuration.

The invention also concerns a hydrocarbon composition comprising any hydrocarbon manufactured using any one of the above or below described processes from any fatty acid or fatty acid derivative sourced from any non-fossil feedstock, characterized by three to twenty-two carbon atoms with any number of double bonds.

A particularly useful group of hydrocarbons forms another part of the present invention: short, medium or long chain alkenes, having one or more double bonds, with either of the general formulae (V):

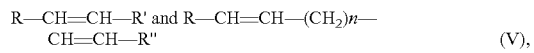

where the double bond has a "cis" or "Z-" configuration, n and the length of the R groups preferably being such that the total number of carbon atoms is from 10 to 21, and R and R' may themselves contain further unsaturations.

Those proficient in the art will, after reading this specification, appreciate the significance of this group of compounds specifically emphasized here, i.e. unsaturated hydrocarbons having 10 to 21 carbon atoms and double bond(s) with cis- or "Z-" configuration. For example, mention may be made of heptadecenes of the general formula $C_{17}H_{34}$, or similar compounds with more than one double bond—at least one of which has cis-configuration—with similar properties.

These compounds differentiate themselves by the distinguished stereo chemistry of that particular middle double bond(s), which is always "cis" or "Z-" (same-sided), while the stereo chemistry of double bonds in refined petroleum feedstock is arbitrary in almost all cases. The hydrocarbons described immediately above, as well as those more generally described by formula (V) can be directly derived by the manufacturing process that forms part of the invention. For instance, some members of the family of hydrocarbons in formula (V) are unsaturated hydrocarbons with 17 carbon atoms, and can be derived from one particular unsaturated fatty acid, namely oleic acid, which is abundant in nature in both vegetable as well as animal fats and oils. The stereo chemistry of its double bond has a very well-defined configuration, practically 100% Z/cis, and the invented manufacturing process preserves this configuration after cleavage of the carboxyl group, reflected in the retained cis-, or "Z-" configuration of the hydrocarbons created. This is of tremendous advantage, as explained below.

This distinguished stereo chemistry leads to a certain preferred spatial molecular "bent" geometry of these compounds, which ultimately lowers their melting point (MP) significantly. This can also be observed in nature in many vegetable oils, which, despite having a fatty acid spectrum that is dominated by $C_{18}$ fatty acids, are liquid at room temperature. Conversely, animal fats with less oleic acid or other unsaturated fatty acids with cis- or "Z-" configuration are solid at room temperature.

Hence hydrocarbons created from natural unsaturated fatty acids using the present process and having 17 or 15 carbon atoms melt far below zero, typically at around −30° C. or lower. At the same time, they are characterized by extremely low volatility and, hence, flammability (i.e. there is far less chance of igniting them accidentally during handling). This may be compared with straight heptadecane ($C_{17}H_{36}$), which has a melting point of 22° C. (72° F.), and would, on its own and without further refining, be practically unusable for diesel and, especially, jet fuel.

Thus, the present C17 alkenes can provide an excellent blend stock for use with conventional jet fuel, and can even stand on there own and replace conventional jet fuel. Those of skill in the art will be aware that jet fuels require lower melting points than previously has been achievable with biofuels. Low melting points are required due to the extended stratospheric flights of jets, and accordingly, extended crossing through regions with very low temperatures.

Manufacturing

A preferred manufacturing process will now be explained, by which, in accordance with the invention, renewable or non-fossil (i.e. not derived from fossilization) feedstocks may be converted into useful hydrocarbons, ethers, or a mix of the two.

The carbon chain in formula (IV) is determined by the type of renewable feedstock being used, and it typically has a chain length between three and twenty-two, depending on the kind of fatty acids that is decarboxylated in the process. For example, palmitic acid ($C_{15}H_{31}COOH$) undergoing the present manufacturing process looses the carboxyl group and turns into pentadecene ($C_{15}H_{30}$), in accordance with formula (VI):

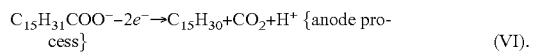

$$C_{15}H_{31}COO^- - 2e^- \rightarrow C_{15}H_{30} + CO_2 + H^+ \{\text{anode process}\} \quad (VI).$$

The melting point of the resulting mixture of pentadecenes is around −6° C., while biodiesel made from palmitic acid melts around +30° C. Moreover, those of skill in the art will appreciate that general melting and boiling ranges correspond to molecular mass. In other words, the choice of chain length is determined in practice by final product requirements (e.g. broad liquid temperature range, low flammability, etc.).

Fuels

The present invention relates to a composition that can be particularly used as a biofuel, the composition comprising one or more of an ether, and a hydrocarbon or a hydrocarbon chain. The ether and the hydrocarbon are preferably in a useful ratio and mixed in liquid form at room temperature. Such a composition and also the compositions described below are particularly suitable as biofuel.

The ether and the hydrocarbon can be mixed in any suitable ratio, preferably from about 1:99 to about 99:1, preferably from about 10:90 to about 90:10, more preferably from about 20:80 to about 80:20, more preferably from about 30:70 to about 70:30, more preferably from about 40:60 to about 60:40 and more preferably about 50:50.

The described hydrocarbon-ether compositions can be used directly as fuel, or they can be processed in a catalytic or other process using, for example, modified alumina ($Al_2O_3$) or similar catalysts at about 350-400° for a specified time, to split the long alkyl off as alkene and to recycle the short-chain alcohol. This can, at the same time, be used to rearrange the long alkyl chain into something more branched using more sophisticated catalysts/conditions, such as those that the person skilled in the art will be aware of.

It is highly desirable to increase the branching of the long alkyl chain and hence lower the melting point of any resulting hydrocarbons longer than thirteen carbons (which have a melting point higher than desirable in a commercial product, especially for jet fuel.

Those of skill in the art will appreciate that, by substituting ubiquitous fatty acids as starting material for a high-performance biofuel, use of the invention directly impacts the alternative use of dwindling supplies of fossil fuels. It will also be appreciated that, by producing carbon-neutral biofuels, use of the invention can directly impact the environment in a positive way by reducing or eliminating carbon emissions. Thus, the invention can preserve fossil fuels while also protecting the environment.

In short, the invented hydrocarbon-ether and hydrocarbon compositions are more similar to conventional petroleum products than is existing biodiesel, whilst being advantageously derived from similar natural and renewable sources, and whilst minimizing emissions of fossil $CO_2$, i.e. whilst maintaining carbon neutrality.

Moreover, the ethers that are produced can, in accordance with one embodiment of the invention, be drawn off using suitable separation techniques, e.g. by fractionation techniques well known to those versed in the arts or any by other suitable process. These materials can stand on their own as biodiesel fuels or can be used as diesel fuel additives (e.g. to improve pour-point or cetane number, or to act as oxygenaters diminishing toxins in engine exhaust, etc.).

Uses for the present compositions include their applications as fuel in any application where petroleum or products are used today. Thus, the present compositions may be similar to those in conventional use, but are made in a different way, from different sources, and have improved properties, e.g. the invented compositions may exhibit naturally ultra-low sulfur, estimated 90+% carbon-neutrality, etc.

BRIEF DESCRIPTION OF THE FIGURE

The FIGURE is a process flow diagram illustrating a manufacturing process of the invention.

It illustrates the present manufacturing process in what is believed to be a largely self-explanatory flow diagram. Fatty/oily feedstock undergoes a fat-splitting process at 200 to split off glycerol to produce pure fatty acid feedstock. Alternatively, pure fatty acid feedstock can be used, as indicated. At 202, non-Kolbe electrolysis produces the novel and useful biofuel of the invention, as described herein, typically including a hydrocarbon-ether mix. Alternatively, the novel biofuel produced by electrolysis undergoes separation, e.g. fractionation, at 204 to produce pure ethers and pure hydrocarbons, as indicated, both of which are useful. Those of skill in the art will appreciate that the ethers can be further processed into pure hydrocarbons, using any suitable process such as cleavage or catalysis, as described herein. The hydrocarbons can be used as diesel, jet fuel, or similar product, or can be conventionally or otherwise suitably refined (at 206) to produce liquid propane gas (LPG), gasoline, or other desired products.

EXAMPLES

The invention will now be illustrated by the following, non-limiting examples. Gas chromatography/mass spectrometry was used to confirm production of an alkene-ether composition suitable for use as a biofuel. The fatty acids used in the examples below have been derived from naturally occurring vegetable oils.

Example I

Pentenes/Methoxypentanes 0.25 mol caproic acid was dissolved in approximately 500 ml 99% methanol and made slightly basic with 105% of the theoretically required amount, using 10% methanolic solution of potassium hydroxide.

This solution was filled up with methanol to produce a 800 ml volume and was poured into a wide reaction vessel of fitting volume equipped with a reflux condenser and two rectangular graphite electrodes approximately 10×10 centimetres in size and of approximately 1-2 mm spacing, connected to a variable DC power supply. The experiment was conducted at room temperature and ambient pressure.

Cooling water was turned on for the condenser, and the voltage was adjusted for a current density of approximately 0.05 A-cm$^{-2}$ electrode surface. Carbon dioxide and hydrogen were evolved while the current was flowing.

An intense scent of pentenes was noticed very shortly after the power was turned on, since pentenes have very low boiling points of approximately 30-40° C.

After approximately 110% of the amount theoretically required, the current was turned off. After cooling to room temperature, the solution was carefully acidified with diluted sulfuric acid and the organic layer formed on top was taken up with ether.

The extract was filtered to remove electrode particles and the solvent was evaporated. Analysis showed a 40-50% content of both possible straight chain pentenes, 40-50% of methoxypentanes and small amounts of n-pentane, esters, alcohols etc.

Example II

Undecenes/Methoxyundecanes 0.2 mol lauric acid was dissolved in approximately 500 ml 99% methanol, made slightly basic with 10% methanolic solution of potassium hydroxide, filled up to 800 ml, and electrolyzed as above, with similar current density etc. as in Example I.

The extract consisted of 44-45% undecenes and 43-44% ethers as follows:

| 1-undecene  | 5%    | 1-methoxyundecane | 10% |
| 2-undecenes | 10%   | 2-methoxyundecane | 16% |
| 3-undecenes | 28%   | 3-methoxyundecane | 16% |
| 4-undecenes | 1%    | 4-methoxyundecane | 1%  |
| 5-undecenes | trace | 5-methoxyundecane | 0.3% |

The undecenes occurred in both E and Z variants in varying amounts. N-undecane, undecanols and dodecanoates were also found in quantities at or below 1%.

Example III

Z, Z/E-Heptadecadienes/Methoxy-Z-Heptadecenes 0.25 mol oleic acid was dissolved in approximately 500 ml technical methanol, made slightly basic with 10% methanolic solution of potassium hydroxide (110% of the theory), filled up to 750 ml, kept at or around 50° C. using a controlled temperature bath and electrolyzed as above, using 120% of the theoretically required current, under similar conditions as in Example I.

The extract consisted of ~75% heptadecadienes, ~20% ethers, and traces of esters etc. The distribution of positional isomers was similar to that in Example II (i.e. the bulk of the isomers were 1,8-, 2,8- and 3,8-E/Z, Z-heptadecadienes, and 1-, 2-, 3-methoxy-Z-heptadecene-8). Those of skill in the art will appreciate from this Example III that heptadecatrienes (characterized by 17 carbon atoms and three double bonds) would be produced using similar techniques to yield similar results, as well as with using lower or higher homologues or more unsaturated acids as feedstock.

The invention claimed is:

1. A process for producing a fuel, which comprises the step of performing electrolysis on an alcoholic solution of a fatty acid or salt thereof or fatty acid ester, to decarboxylate said fatty acid or said salt or said fatty acid ester, and produce a mixture of an ether and an alkene, wherein the electrolysis is performed using a current density of 0.02 to 0.15 Acm$^{-2}$ and a voltage of less than 15V.

2. A process according to claim 1, wherein the total concentration of the fatty acid or said salt or said fatty acid ester in the alcoholic solution is at least 0.5 M.

3. A process according to claim 1, wherein the alcoholic solution of the fatty acid or said salt or said fatty acid ester, comprises an alkali metal or alkaline earth metal hydroxide salt.

4. A process according to claim 1, wherein the electrolysis is performed at substantially the reflux temperature of the alcoholic solvent.

5. A process according to claim 1, wherein the electrolysis is performed using an anode and a cathode, wherein the anode and cathode are composed of materials that are the same as or different from one another and each independently comprises one or more of carbon, platinum, steel, copper, silver, gold and nickel.

6. A process according to claim 1, wherein the electrolysis is performed in an apparatus having an anode and cathode, and wherein the closest spacing between the anode and cathode in the alcoholic solution is from 0.5 to 5 mm.

7. A process according to claim 1, wherein said fatty acid comprises a monounsaturated fatty acid and the electrolysis is performed on said monounsaturated fatty acid.

8. A process according to claim 1, further comprising the step of separating the alkene and ether from the alcoholic solution.

9. A process according to claim 1, wherein the electrolysis is performed using a current density of 0.06 to 0.09 Acm$^{-2}$ and a voltage of less than 12V.

10. A process according to claim 1, wherein the total concentration of said fatty acid said salt thereof or said fatty acid or ester in the alcoholic solution is at least 0.8M.

11. A process according to claim 1, wherein the ratio of the ether to the alkene in said mixture is in the range of from 30:70 to 70:30.

* * * * *